(12) United States Patent
Chan et al.

(10) Patent No.: US 11,089,743 B2
(45) Date of Patent: Aug. 17, 2021

(54) SYSTEM AND METHOD FOR DETERMINING TURF PERFORMANCE INDICATORS

(71) Applicant: STEVENS WATER MONITORING SYSTEMS, INC., Portland, OR (US)

(72) Inventors: Chun Kit Chan, Clackamas, OR (US); Michael Kuvelas, Vancouver, WA (US); Carmen Magro, Wynnewood, PA (US); Scott South, Vancouver, WA (US)

(73) Assignee: Stevens Water Monitoring Systems, Inc., Portland, OR (US)

( * ) Notice: Subject to any disclaimer, the term of this patent is extended or adjusted under 35 U.S.C. 154(b) by 0 days.

(21) Appl. No.: 15/441,023

(22) Filed: Feb. 23, 2017

(65) Prior Publication Data

US 2017/0241923 A1  Aug. 24, 2017
US 2017/0363551 A9  Dec. 21, 2017

Related U.S. Application Data

(60) Provisional application No. 62/298,891, filed on Feb. 23, 2016.

(51) Int. Cl.
*A01G 22/00* (2018.01)
*G01N 33/24* (2006.01)
*A01G 20/00* (2018.01)

(52) U.S. Cl.
CPC ............. *A01G 22/00* (2018.02); *A01G 20/00* (2018.02); *G01N 33/246* (2013.01)

(58) Field of Classification Search
None
See application file for complete search history.

(56) References Cited

U.S. PATENT DOCUMENTS

| 4,192,510 | A | 3/1980 | Miller |
| 5,668,306 | A | 9/1997 | Doherty et al. |
| 5,736,631 | A | 4/1998 | Dixon et al. |
| 5,886,253 | A | 3/1999 | Joustra et al. |
| D418,073 | S | 12/1999 | Kreutzer et al. |
| 6,171,199 | B1 | 1/2001 | Cohodas |
| 6,601,440 | B1 | 8/2003 | Chuang et al. |
| 6,826,972 | B2 | 12/2004 | Clark et al. |
| 7,106,076 | B2 | 9/2006 | Tillmann et al. |

(Continued)

*Primary Examiner* — Curtis A Kuntz
*Assistant Examiner* — Shawna M Kingston
(74) *Attorney, Agent, or Firm* — FisherBroyles LLP; Kevin D. Jablonski

(57) ABSTRACT

System and method for quantifying qualitative turf conditions as they relate to turf performance and health. In an embodiment, data is collected about turf condition using a turf analysis device. The data collected about the conditions may be used to generate condition-based turf stress indexes that may be used to generate an overall a Turf Performance Indicator (TPI). Such collections are calculated through a unique quantitative mathematical equation resulting in a measurable quotient that is used to assess overall turf performance qualities on a relative scale over time. Using an integrated Global Positioning System (GPS), the TPI measurements can be used to identify overall property conditions and zone specific conditions within that property. Such analysis is viewed with visual analysis methods using a cloud based system.

16 Claims, 5 Drawing Sheets

(56) References Cited

U.S. PATENT DOCUMENTS

| | | |
|---|---|---|
| D616,314 S | 5/2010 | Akomolede et al. |
| 8,656,759 B2 | 2/2014 | Hughes et al. |
| 9,952,327 B2 | 4/2018 | Schultz |
| 2005/0024213 A1 | 2/2005 | Franzen et al. |
| 2011/0203356 A1 | 8/2011 | Scherbring |
| 2012/0084115 A1* | 4/2012 | Cline ............... A01G 25/16 705/7.27 |
| 2012/0109387 A1* | 5/2012 | Martin ............ A01G 25/167 700/284 |
| 2013/0308426 A1 | 11/2013 | Scarlatti et al. |
| 2014/0035752 A1* | 2/2014 | Johnson ........... A01B 79/005 340/601 |
| 2015/0309496 A1* | 10/2015 | Kah, III ............. A01G 22/00 700/284 |
| 2015/0323491 A1 | 11/2015 | Miller et al. |

* cited by examiner

SYSTEM AND METHOD FOR DETERMINING TURF PERFORMANCE INDICATORS

PRIORITY CLAIM AND CROSS REFERENCES TO RELATED APPLICATIONS

The present application claims priority and benefit from the U.S. Provisional Patent Application No. 62/298,891, filed Feb. 23, 2016 and titled, "SYSTEM AND METHOD FOR DETERMINING TURF PERFORMANCE INDICATORS". The entire content of the provisional application is herein expressly incorporated by reference. Further, the present application refers a commonly-assigned U.S. patent application Ser. No. 15/441,015, entitled "SYSTEM AND METHOD FOR TRACKING AND OPTIMIZING PINHOLE LOCATIONS ON A PUTTING GREEN" filed on Feb. 23, 2017, and commonly-assigned U.S. patent application Ser. No. 15/440,998, entitled "SYSTEM AND METHOD FOR INSTANTANEOUSLY DETERMINING UNIFORM DISTRIBUTION OF WATER, SALINITY, CONDUCTIVITY, TEMPERATURE AND OTHER CONDITIONS IN SOIL" filed on Feb. 23, 2017, the disclosures of which are incorporated by reference.

BACKGROUND

Golf is a sport enjoyed by millions of people the world over. Its popularity indicates that interest in golf remains vibrant and growing. As a result, groundskeepers (which include golf course greenkeepers and superintendents) are always seeking to enhance the playing experience for golfers while increasing efficiencies in maintaining turf including fairways, putting greens and other areas of the golf course property in additions to sports fields, parks, and other land covered in grass turf. Many variables may affect turf quality including moisture content, water retention and drainage, soil contents and conditions, salinity influences, weather, and use patterns. Thus, groundskeeper are continuously monitoring various conditions in an effort to maintain or improve the quality of the turf.

One particular area in which groundskeepers are keenly aware of involves overall turf quality both on putting greens and in fairways. Many factors may be used to determine overall turf quality. These factors include relative hardness, moisture content, resilience, temperature, conductivity, salinity, and the like. However, in addition to years of education, groundskeepers typically hone their craft through years of trial and error experience such that a feel for the turf may be developed. Of course, the "feel" may differ from course to course and from groundskeeper to groundskeeper. Conventional golf course maintenance does not have any objective, standard, or measurable indicators. Turf performance indicators (TPI) may be used to determine the overall performance quality of the turfgrass system.

BRIEF DESCRIPTION OF THE DRAWINGS

Aspects and many of the attendant advantages of the claims will become more readily appreciated as the same become better understood by reference to the following detailed description, when taken in conjunction with the accompanying drawings, wherein:

Note that the same numbers are used throughout the disclosure and figures to reference like components and features.

DETAILED DESCRIPTION

The subject matter of embodiments disclosed herein is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Embodiments will be described more fully hereinafter with reference to the accompanying drawings, which form a part hereof, and which show, by way of illustration, exemplary embodiments by which the systems and methods described herein may be practiced. This systems and methods may, however, be embodied in many different forms and should not be construed as limited to the embodiments set forth herein; rather, these embodiments are provided so that this disclosure will satisfy the statutory requirements and convey the scope of the subject matter to those skilled in the art.

By way of overview, the subject matter disclosed herein may be directed to systems, apparatuses, and methods for using a turf analysis device for determining various factors and variables in turf across one or more turf locations. From the collected data, a turf analysis procedure may be implemented to determine an overall turf performance indicator. Further lab analytics and additional algorithms for assessing specific factors of turf may be implemented based on the initial collected data. All data may be assimilated into a database and compared against previous data collections from earlier in time as well as previous collections of data from other locations of turf. By developing one or more repeatable and reliable indicators of turf quality, a groundskeeper may implement specific factor-based solutions to improve turf quality. These and other advantages will become more apparent in the detailed descriptions below with respect to FIGS. 1-5.

Figure 1:
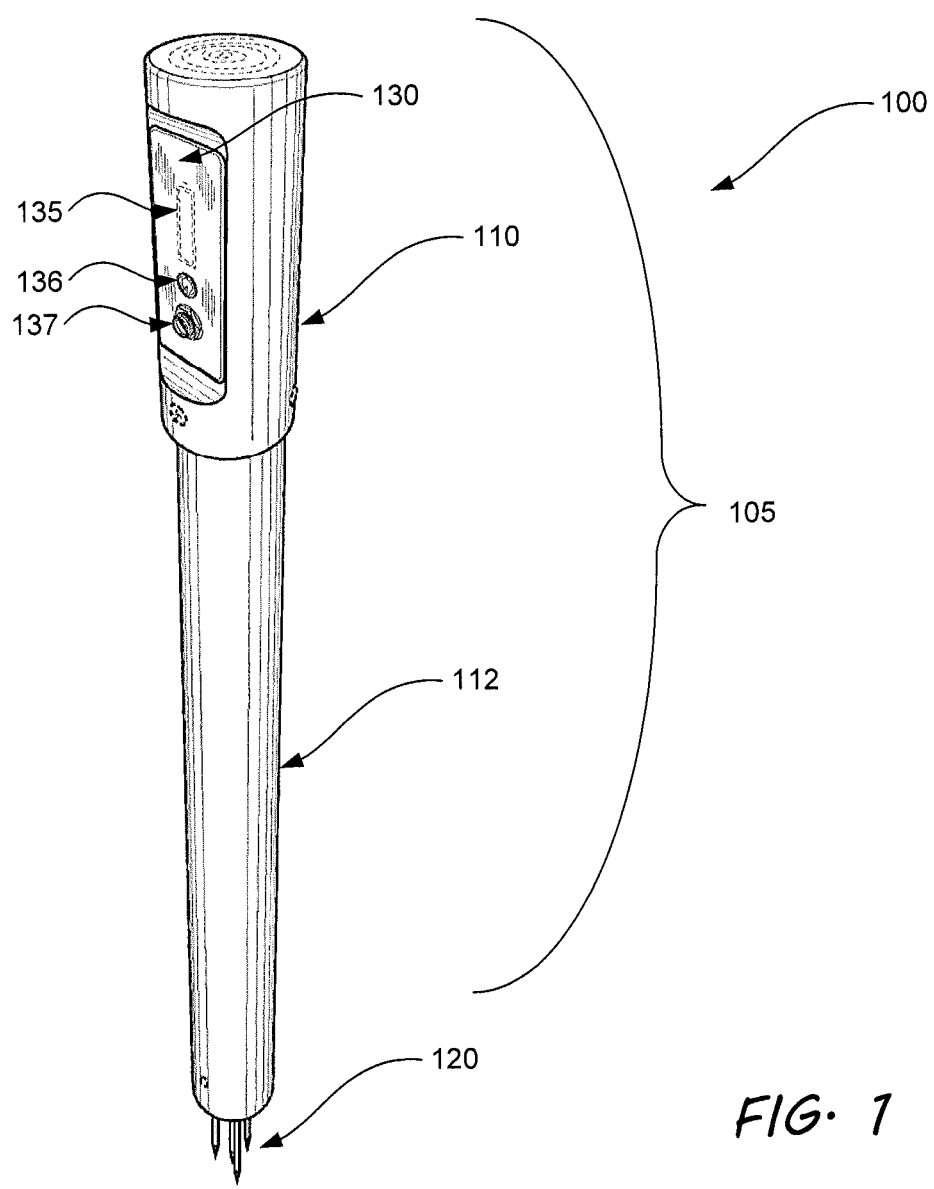
FIG. 1 is a device for performing turf analysis according to an embodiment of the subject matter disclosed herein.

FIG. 1 is a diagram of a turf analysis device for collecting data for turf quality analysis according to an embodiment of the subject matter disclosed herein. The device 100 may be embodied in an elongated housing 105 that may be cylindrical in nature. The housing 105 may include an upper portion 110 that is slightly larger in circumference than a lower portion 112. The lower portion 112 may be tapered. Below the surface of the flat area 112 is a rechargeable battery for providing power to the device 100. The housing may have a length of between six inches and three feet.

The housing includes four prongs 120 at a bottom end. The four prongs 120 include a pointed end designed to penetrate the surface of turf, such as a putting green or a fairway. The prongs may be conductively coupled to integrated electronics (not shown in FIG. 1) in the interior of the device 100. The prongs coupled with the integrated electronics become a multi-parameter sensor to determine specific physical aspects of the turf, such as water content, conductivity, salinity, temperature, and the like. When the prongs 120 are engaged with the turf, the device 100 may stand upright on its own.

The upper portion 110 may include a flat area 130 that contains various input and output functionality for the device. The flat area 130 may include a removable cover for engaging or disengaging an underlying battery (not shown), a communication module 220, a processor 210, and a GPS module 225 (all shown in FIG. 2).

The flat area 130 may, in and of itself, be a display 135 (such as an LED display, for example) for displaying data such as the data being collected. The display 135 may show additional data such as coordinates of the current location and battery life remaining. The flat area 130 may include a software-based or hardware-based power button 136 for turning the device 100 on and off. The flat area 130 may include an interface 137 for recharging the battery. Additional features of the device 100 are shown in the block diagram of FIG. 2.

Figure 2:
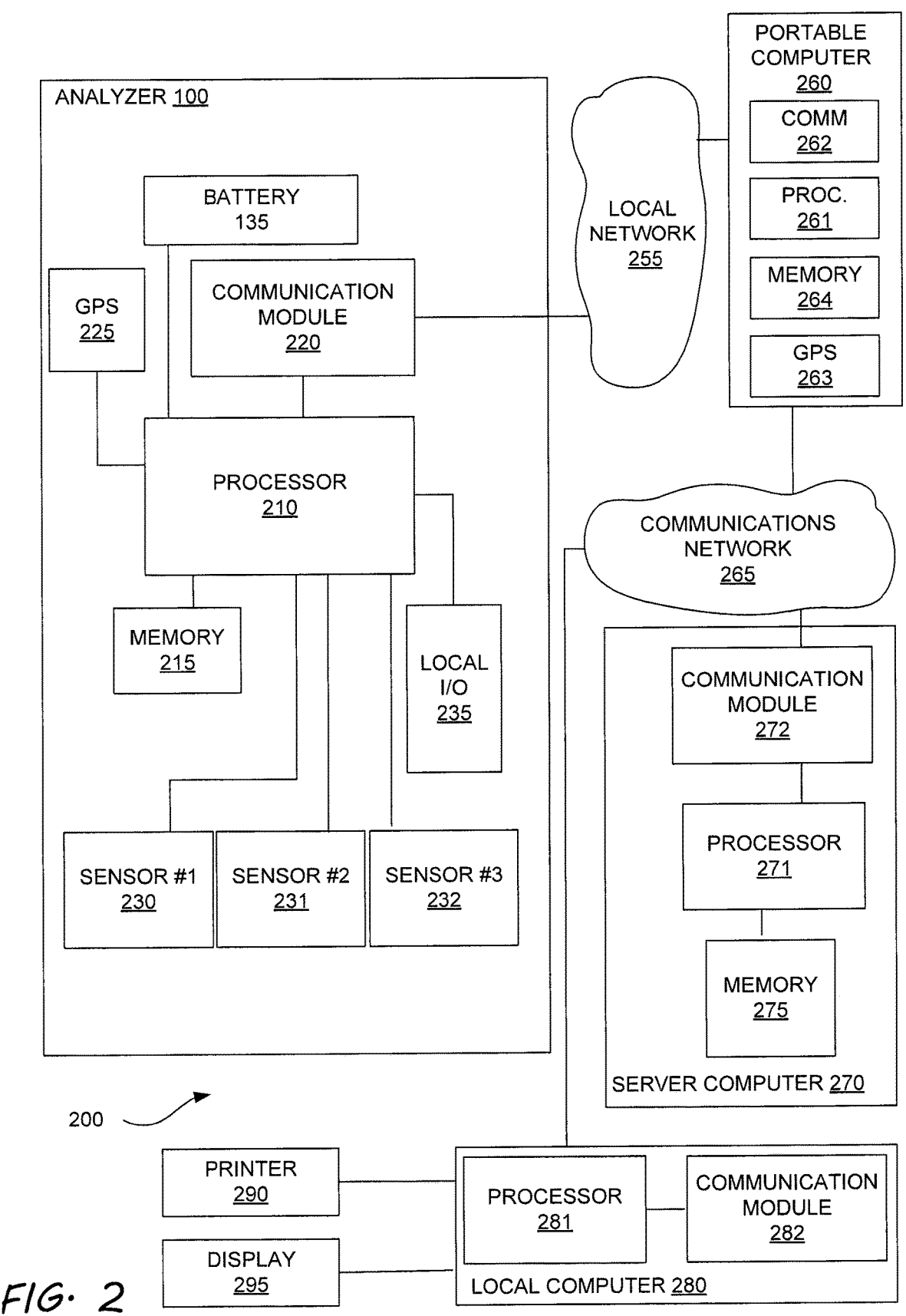
FIG. 2 is a system for using the turf analysis device of FIG. 1, according to an embodiment of the subject matter disclosed herein.

FIG. 2 is a system 200 for using the turf analysis device 100 of FIG. 1, according to an embodiment of the subject matter disclosed herein. The system 200 includes the turf analysis device 100, a local portable computing device 260, and a server computer 270, and a local computer 280 that may be coupled to an external display 290 and a printer 295. As briefly mentioned above, the turf analysis device 100 includes a processor 210 and a local memory 215 that may store instructions that may be executed by the processor 210. Further, local I/O 235 is coupled to the processor and may be a power button or a display as discussed above. The processor and other components may be coupled to the battery 135 for provision of power.

In this embodiment, there are three sensors 230, 231, and 232 shown for obtaining various sensor measurements but there may be more or fewer depending on application and model. The sensors 230, 231, and 232 may include probes, embodied in the prongs 120 of FIG. 1 for engaging with turf surface and soil below the surface of turf. The multi-parameter sensors may include a soil analysis sensor, and electric conductivity sensor, a soil moisture sensor, a temperature sensor, or any other sensors that may be useful in determining data about soil or turf.

The turf analysis device 100 includes various interfaces for engaging exterior computer networks. A first interface is a communication module 220, which may be communicatively coupled to communication module 262 for providing a communication link between the turf analysis device 100 and to one or more remote computing devices, such as portable computer 260, through a local communication network 255. In one embodiment, the communication modules 220 and 262 may be a wireless network adapter for WiFi interconnectivity using IEEE-802.xx standards and TCP/IP protocol. In other embodiments, the communication modules 220 and 262 may be a short-range network module for using BlueTooth™ and the like. In still further embodiments, the communication modules 220 and 262 may be a cellular network device for engaging one or more Long-Term Evolution (LTE), e.g., cellular, networks. These communication modules 220 and 262 may communicate through a local communication network 255 as discussed in the embodiments above.

Another interface for engaging another computer network is the global position system (GPS) module 225. The GPS module 225 may be configured to engage the GPS whereby a space-based navigation system provides location, altitude, and time information in all weather conditions anywhere on or near the Earth when the device can connect to a computer network where there is an unobstructed line of sight to four or more GPS satellites determining location. The GPS module 225 may link directly to the GPS satellite network or may link to other networks (such as an LTE network). The GPS module 225 provides data, typically in the form of longitudinal and latitudinal coordinates as well as altitude in terms of distance from sea level. The GPS data may be assimilated with sensor data by the processor 210 and then communicated via the communication module 220 to the local remote portable computer 260. The GPS data may also be assimilated by portable computer 260 that have integrated GPS module 263.

The portable computer may be any number of mobile computing devices such as a smart phone, a tablet, a laptop computer and the like. The portable computer 260 may typically include one or more local processors 261, a local communication module 262, a GPS module 263, and memory 264 for sending, receiving and storing data as well as execution applications. Local memory 264 may store instructions that may be executed by the processor 210 and the turf analysis device 100. The portable computer may also include an integrated GPS 263, battery (not shown), and display (not shown). The memory 264 may also store data (e.g., sensor measurements) collected by various sensors 230, 231, and 232; data collected from the GPS module 225 or 263; and battery health conditions. In the system 200 of FIG. 2, the portable computer 260 may be configured to execute a turf quality analysis application to be used in conjunction with the turf analysis device 100.

The turf quality analysis application may track and locally store data (in memory 264) about locations in turf under analysis and link GPS location to the application using an integrated GPS radio or application for wirelessly linking to a more accurate GPS location device. The application may be configured to log analyzed locations and automatically link such location information to a centralized software program. The logged information includes collected sensor data, date, time, latitude, longitude, altitude, picture and/or electronic notes inputted by user for each turf quality analysis location. The application may also track historical trending of turf quality analysis locations. Such historical location information is selectable by user. The application may be configured to guide and warn a groundskeeper of optimal turf quality. Further, the application provides a means for administrative reporting of turf quality analysis locations for a golf course that may be used to improve management of turf quality and conditions and may be used to update a course map in a clubhouse.

Upon collection of enough historical data, the application may be used to animate turf quality over user defined data history that is viewable on-line via software as a service platform. Further, the current turf quality may be overlaid on a Geographic Information System (GIS) location satellite image with various selectable layers for visual analysis and comparisons among many different locations.

The system 200 may further include a server computer for storing data collected remotely and for assimilating turf quality data over the course of time. The server computer 270 may be communicatively coupled to the portable computer 260 and to a local computer 280 through various means using the communication network 265. Thus, the application(s) discussed above may be cloud-based utilizing a server processor 271 having a local memory 275 through a local communications module 272.

The system 200 may include a printer 290 interfaced with the local computer 280 for printing turf quality analysis reports and maps. One or more application may include a printing program that is linked to each golf course golf hole and respective turf quality analysis data based on the most recently logged GPS location. Integrating the turf quality analysis data with a cloud-based service for controlling the printer 290 enables the golf course club house to print customized score cards that show the current turf quality for the day and enables golfers to printout the turf quality at any printer prior to arriving at the golf course. Further, additional data may be printed on golf card or displayed at the display 295, such as historical pin locations and respective effects on handicap, players' names, players' handicaps, marketing information from the golf course, current weather conditions and forecast, and the like.

Figure 3:
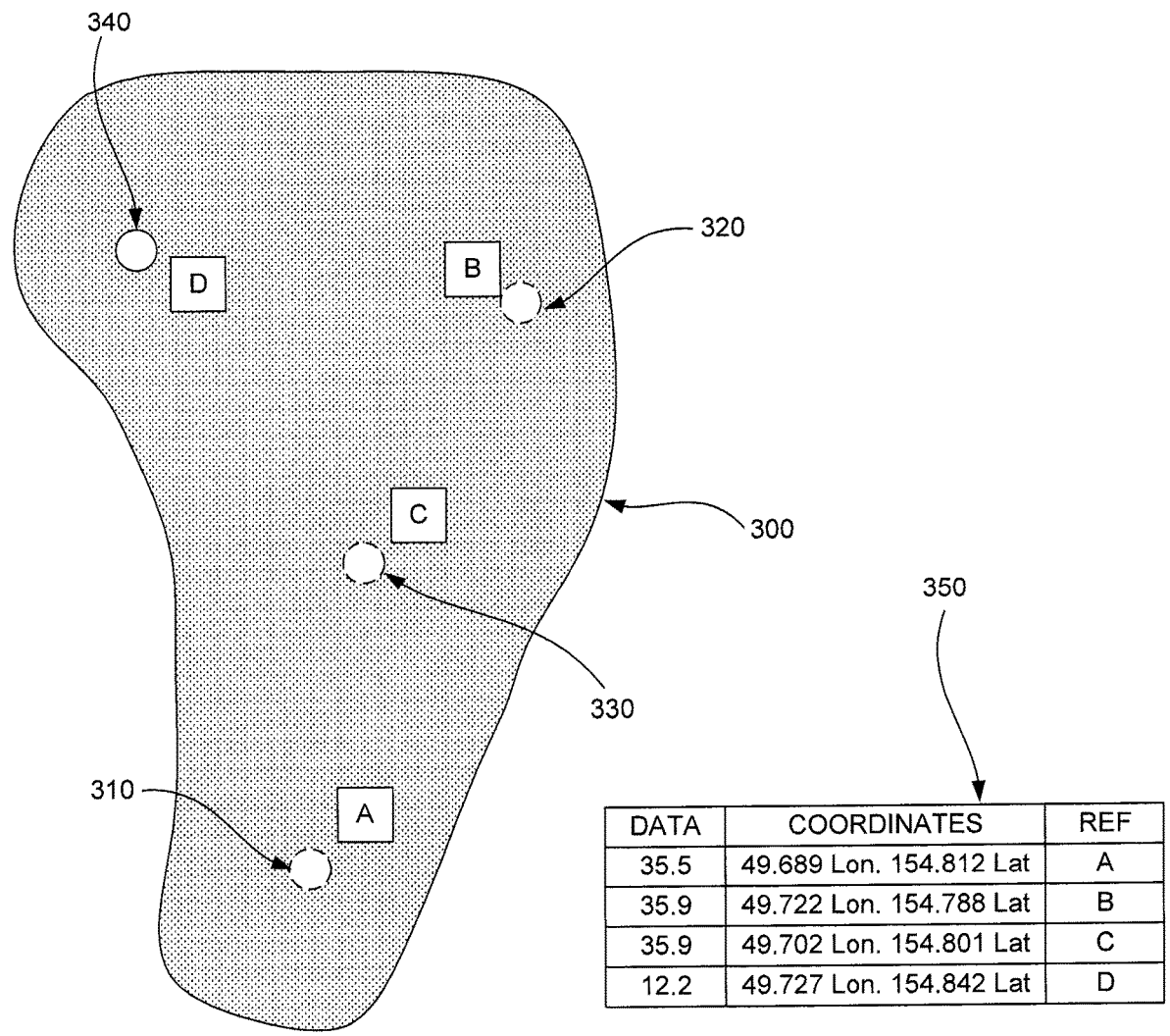
FIG. 3 is a diagram illustrating a screen shot showing a putting green 300 having various turf analysis locations along with turf analysis data according to an embodiment of the subject matter disclosed herein.

FIG. 3 is a diagram illustrating a putting green 300 having various turf analysis locations along with turf analysis data according to an embodiment of the subject matter disclosed herein. Such a view may be displayed on a display at any computer such that a user may utilize and interact with data collected and to be collected by a turf analysis device 100. In this illustration, a putting green 300 is shown; however, any depiction of turf may be rendered such as a fairway, sports field, or even a simple block diagram showing regions of turf to be analyzed. Further, the putting green shows four turf analysis locations. There may be many more in a typical analysis, but four are illustrated here for the purposes of this embodiment. The four locations correspond to references A 310, B, 320, C, 330, and D 340. The locations may correspond to actual locations in which the turf analysis device 100 was used to determine specific factors (e.g., data collected) about the turf. These factors may be assimilated into a turf analysis algorithm (discussed below) to determine an overall turf quality indicator known as turf performance indicator (TPI). These turf performance indicators may be displayed in a table 350.

Turf performance, in and of itself, may be the result of several factors. The factors may be determined using a turf analysis device 100 within a turf and soil insight system. The collection of data about the various factors makes it possible to effectively measure key variables that indicate turf performance and turf stress to be assessed for current and/or trending conditions. In addition, lab analytics can be used to indicate key characteristics that become very powerful indicators when combined with in situ measurements of key variables of the turf. In an effort to assess the turf performance quality of any turf grass system, several variables (sometimes called stresses) may be individually measured and then used to tailor lab analytics to include key assessments associated with understanding what monitored measurements mean as far as their insight to true turf conditions. In one embodiment, an algebraic equation may be used to assess the performance of a turf system against any one turf variable/stress. Such an equation yields a Turf Stress Index (TSI) that is associated with the specific variable being measured. Further, using a weighted formula, one may combine the effects of several stresses to indicate a Turf Performance Indicator (TPI) score, which is an indication of turfgrass performance as a whole. That is, several TSIs may be combined to generate an overall TPI.

The formulas are written to allow the optimum levels to be customized while taking into account tolerance factors for each variable. The data collected may be assimilated into an analysis application to keep track of real time measurements using one or more stationary sensor systems. Further, the application may assimilate data collected from measured variable or ratio of variables captured from portable monitoring, in-ground monitoring, lab analysis, or observational measurements that are made scientifically and practically.

The individual TSI calculation can be applied to any number of variables that can be recorded from the turf analysis device 100, a turf analysis weather station, other soil sensors, lab analysis reports, and any other variable where a comparison of the actual versus the optimum can be made. The formula takes into account several factors that influence turfgrass performance. The various stresses that can be measured include soil moisture, soil salinity (sometimes called electrical conductivity (EC)), ambient temperature, canopy temperature, and EC/moisture ratio.

The Turf Stress Indicator (TSI) calculation for a single variable is $$TSI=100/[(e0.5(x-xo/TOL)2]Var1$$

In this formula, the variables are: TSI=Turf Stress Indicator where 100 is the least likelihood for the particular stress; zero is the highest likelihood. The TPI may be thought of as the turf's strength against a particular stress. So a score of 100% means the turf is likely not under any pressure from that stress, or variable.

Another variable is e=mathematical constant of 2.71828 which is approximately the base of the natural logarithm. Another variable is x=measured variable of interest (moisture, salinity, temperature, (EC/moisture ratio, and the like). Another variable is xo=optimum value for the variable of interest (user' definable and determined from a large network of users and collected data, customizable per customer's tolerances and key property or zone attributes determined from observations or lab analysis). Another variable is TOL=a defined tolerance factor for each measureable variable essentially defining the delta around an optimum value (i.e., if optimum salinity is 0.21 dS/m and it is desired to allow a range of 0.15 to 0.27, TOL would be 0.12). Again, this is customizable and unique.

In a spreadsheet, the formula will look like that below and will not only calculate the TSI but will indicate whether the value is below (indicated by a negative value) or above the optimum level. This is important for several variables. For instance, if moisture has a 70% stress performance score, it may be important to know if it is too moist (positive value) or too dry (negative value) causing this less than optimum condition.

TSI (Spreadsheet Language): $=(100/2.71828^{\wedge}(0.5*((B3-A3)/C3)^{\wedge}2))$ Where:
B3 is a column assignment for measured condition
A3 is the column assignment for the optimum condition
C3 is the column assignment for the TOL factor
To determine whether the value is to the positive or negative size of optimum, a reference to the actual measured value minus the optimum value is made before combining the +/− symbol to the calculated TSI Value.

Positive or Negative (+/−) value determination
(Spreadsheet Language): $=IF(B3-A3<0,"-","+")$ Where:

B3 is the column assignment for the measured condition

A3 is the column assignment for the optimum condition

Note that '+' is assigned to 0 values and above and '−' values are assigned to <0 values.

Turf Performance Indicator (Moisture, Salinity (EC), Temperature)

To calculate the performance of a turf system, several factors may be considered. For instance, if there is a moisture stress with limited salinity (EC) stress, then one level of turf performance exists. If there is the same turf system with low moisture stress but increased salinity stress, then another turf performance condition exists. If there are elevated moisture and salinity stresses, then an entirely different turfgrass performance level exists. This can be the case for any number of variables. The three most easily ascertained, and which are three of the most influential variables on turf performance, include moisture, salinity (EC), and temperature. Further, with regard to temperature in particular, turf canopy, or surface temperature is a direct measurement of temperature's influence on turf stress. The turf analysis device 100 directly measures these variables using research grade multi-parameter sensors requiring no calibration in any turf/soil type. This makes the repeated capturing of these variables easy and applicable to apply these calculations to understand how well the turf system is performing at any given time. The consistent measurements of research grade multi-parameter sensors results in a universally comparable TPI value using different turf analysis devices and across many geographically locations. For example, a golf course in one geographical region can compare the TPI to another golf course in a separate geographical region.

However, even when measured variable conditions are optimal, turf performance can be suffering from external influences not directly measurable. For example, pathogenic fungi can be invading a particular turf plot and causing disease decline even when temperature, moisture and salinity measurements are not indicating there is a problem. Pathogenic fungi are influenced by increased heat and moisture, but the attack on turf plants is not necessarily increased due to this. The recovery of the turf, however, is directly related to the turf's performance at the time of disease onset. Therefore, having knowledge of turf performance indicators or having a quantitative value to associate with a qualitative condition has application in disease likelihood assessment or any other ailment that can result in turf decline.

Despite this fact that problems can still occur even when conditions seem optimal for good turf performance, using a customized visual analysis of the conditions may allow the input of a number indicating such visual appearance into the turf performance indicator calculation allowing for a measurement of the overall turf performance to include a visual inspection. Generally speaking, when the TPI is high (>85%), turf performance is generally acceptable and least likely to develop conditions leading to declined performance.

By combining several Turf Stress Indicator results with weights to their influences applied, a weighted average Turf Performance Indicator can be calculated. Using a weighted average formula where this formula above would be calculated for any number of variables (e.g., salinity, moisture, temperature, ambient temp/humidity, traffic, and the like) and each of those variables are assigned a weighted value from 1 to 5 for instance, a summation of the result of multiplying each individual TSI by the weighted value and then dividing that total by the sum of all of the weighted values is calculated. There is now a total weighted average TPI on the same 0 to 100 scale indicating the overall TPI of the turf (or crop, land stress, runoff potential, etc.). While the weighted average values are being assessed with much data being collected over the past years and moving forward, the initial formula treats each variable equally. However, here is the weighted average formula written out:

Turf Performance Index$_{WAvg}$={(100/[($e0.5(x-x0/TOL)2$])$_{TSI\,1}$+(100/[($e0.5(x-x0/TOL)2$])$_{TSI\,2}$+(100/[($e0.5(x-x0/TOL)2$])$_{TSI\,3}$+TSI $n$ calculations}/(Weighted valueTSI1+Weighted valueTSI2+Weighted valueTSI3+Weighted value TSI $n$)

In a first phase, all variables are given equal weight, where n is the number of individual TSI's calculated, the Turf Performance Indicator without weighted averages applied would be:

TPI={100/[($e0.5(x-xo/TOL)2$])$_{TSI\,1}$+100/[($e0.5(x-xo/TOL)2$])$_{TSI\,2}$+100/[($e0.5(x-xo/TOL)2$])$_{TSI\,3}$+100/[($e0.5(x-xo/TOL)2$])$_{TSI\,n}$}

The more TSI values inputted to the calculation, the more representative the calculation will be to include as many influencing variables as possible. A TPI report is used to summarize a report card for multiple TSIs as they relate to turf performance while giving insight to individual 'scores' that will direct attention to any one variable.

The resulting TPI factor of the above combines the results of several variables into a quantitative analysis of the overall performance potential of a system called the Turf Performance Indicator. This calculation is implemented utilizing a database such as the turf analysis system 200, and then the resulting determinations are relayed in near real time through the turf analysis application and cloud-based computing system. The turf analysis device 100 itself is unique so this calculation is truly unique and based upon the value of much recorded data from turf systems around the globe.

From a practical perspective, users can input respective tolerances and simply view the TPI at any given time to know where their system is from zone to zone, property to property (in the case of management companies and multi-facility operations), or from period to period. At no time does a user have to dive into this calculation. The proprietary nature of the calculation is done in the background while the user may adjust the optimum level and log conditions.

The effects of EC and moisture together have multiple effects that influence turfgrass performance. It is not always enough to simply look at the moisture and salinity levels without understanding the relationship of these to each other. A ratio of EC to moisture, for instance, indicates the concentration of salts to a given amount of water. This is insightful to understand salinity issues besides just having elevated salts in the turf system. A calculation to understand this involves dividing the EC by moisture. Both would have to be in decimal format with moisture being reported as a decimal percentage water fraction volume (i.e., 0.22=22% moisture by water fraction volume (wfv)). Salinity (EC) on the other hand would be reported to two decimal places as well but reporting in deciSiemens per meter (dS/m) such as 0.65 dS/m. In this case, our EC/Moisture ratio would be 0.65/0.22=2.95. This is a unique way of determining the concentration of EC to moisture. This example calculation shows a very high EC/Moisture ratio indicating a high salinity concentration for a fairly low amount of moisture. Ideally in turf, the ratio should be around 1.00. However, with the increased demand to use reclaimed and effluent water sources on turf in particular, salinity levels are at an all-time high. This ratio must be considered in a turf system to truly understand turf performance levels at any given time.

Another TSI to be considered includes measuring the effects of temperature and moisture together. In particular, as canopy temperature rises above an optimum level, stresses set in that are influenced by that temperature. As moisture climbs above an optimum level, moisture has a particular impact on turf performance as well. However, when both temperature and moisture rise above their optimum levels, the combination of the two have a much more negative influence on turf performance. To effectively measure this initially, a calculation measuring the points away from optimum for both variables combines these results to get a total departure from the two together and indicating the stress that this combination causes.

For example, if an optimum temperature level is 78 degrees F. and the turf is at 88 degrees in the canopy (measured by the turf analysis device 100), a 10-point variance from optimum is recorded. In addition, if the optimum moisture value is 0.25 wfv, or 25% wfv, and a turf value at 0.38, or 38% wfv, then there is a 13-point variance from optimum for moisture. The combined effects of these would be 23 points from optimum. This is one way to measure the effects of the two variables together. More complex forms of this calculation are possible as more and more data is collected from the turf analysis system from turf systems around the world.

Lab Analytics may be used in turfgrass and agronomy applications for understanding soil influences or water, tissue, pathogenic fungi, and microbiological influences as well. One particular way to use lab analytics here is to develop a turf analysis Soil Health Report. In this report, some specific information is ascertained to understand what the optimal levels are for the particular soil being tested. Each turf analysis 'zone' that is identified at a particular property will have different specific conditions only identified by this analysis.

The variables that are recorded may be used in a logarithmic assessment and have applied optimum levels based on user-determined algorithms. These optimum levels drive how far away from optimum the condition is. In addition to this, a Saturation Percentage may be determined indicating how much water an equal part of soil takes to saturate, or reach field capacity. In one embodiment, an ideal condition for a particular soil and for a quality turfgrass surface may be achieved when the user can maintain a moisture percentage (wfv) that is 40% of the saturation percentage. The measurement may be further refined to include a bulk density of the sample that indicates whether a dense layer exists in the turf system or not. Soil tests may not identify the existence of such a layer despite the fact that these layers are very detrimental to turf systems and have a significant impact on water holding and salinity holding capacities of the turf system as whole. This analysis overcomes these issues. Additional report guidelines are contemplated.

Figure 4:
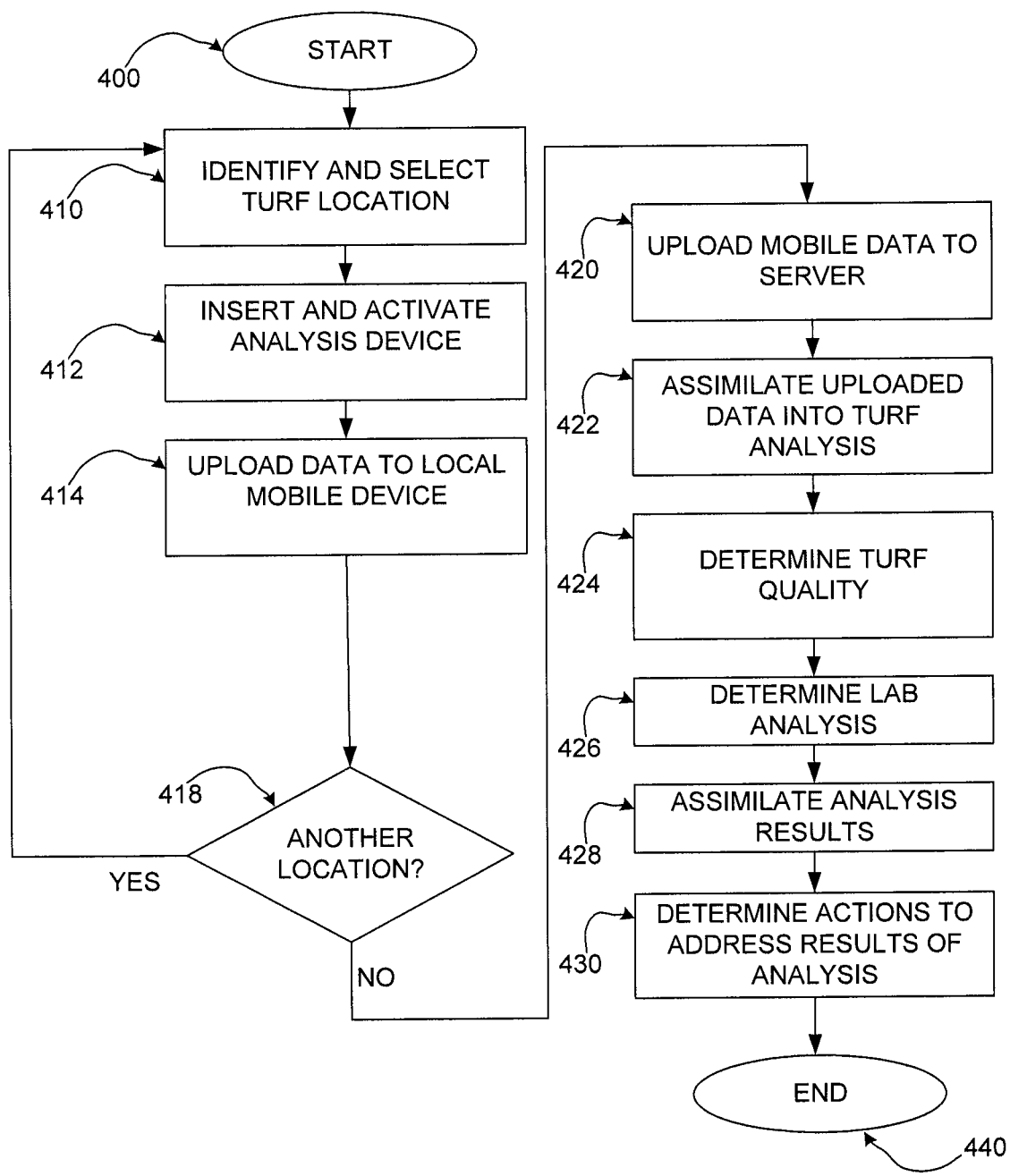
FIG. 4 is a flow chart of a method for determining and using turf quality indicators for turf under analysis.

FIG. 4 is a flow chart of a method for determining and using turf performance quality indicators for turf under analysis according to an embodiment of the subject matter discussed herein. The method may start at 400. A user of a turf analysis device 100 may begin collecting field data by identifying and selecting specific turf locations to analyze at 410. Once a turf location is selected, the turf analysis device may be inserted in the turf and activated at 412. At 414, the turf analysis device collects and determines one or more data points about the underlying turf at 412. At 414, the turf analysis device may store the data locally or upload the data to a nearby portable computing device that may be executing a turf analysis application. At 416, the local mobile device may display the collected data measures with the turf analysis device 100 and present the average of soil measurements within the specific turf location to provide an immediate visual turf performance conditions. At 418, a determination is made as to whether additional turf locations are to be analyzed. If yes, the method loops back to 410. If no, the user may proceed to 420.

At 420, the locally collected data may be uploaded to a server computer for further analysis and assimilation. Once uploaded, the data may be used in a series of algorithms at step 422 to determine specific indicators about overall turf quality as discussed above. The indicators may then be used to determine an overall turf quality at 424. Additionally, lab analysis of turf samples may be used to determine additional indicators about the turf at step 426. Then all indicators determined from direct lab analytics or algorithmic indicators may be assimilated in a set of overall results at 428. Based on the overall results, specific actions may be recommended or taken at step 430.

Additional steps may be implemented that utilize additional information such as turf analysis or may discount some data because of anomalies. Further, the steps of the method in FIG. 4 may be implemented in any order and not necessarily the order presented in the embodiment of FIG. 4.

Figure 5:
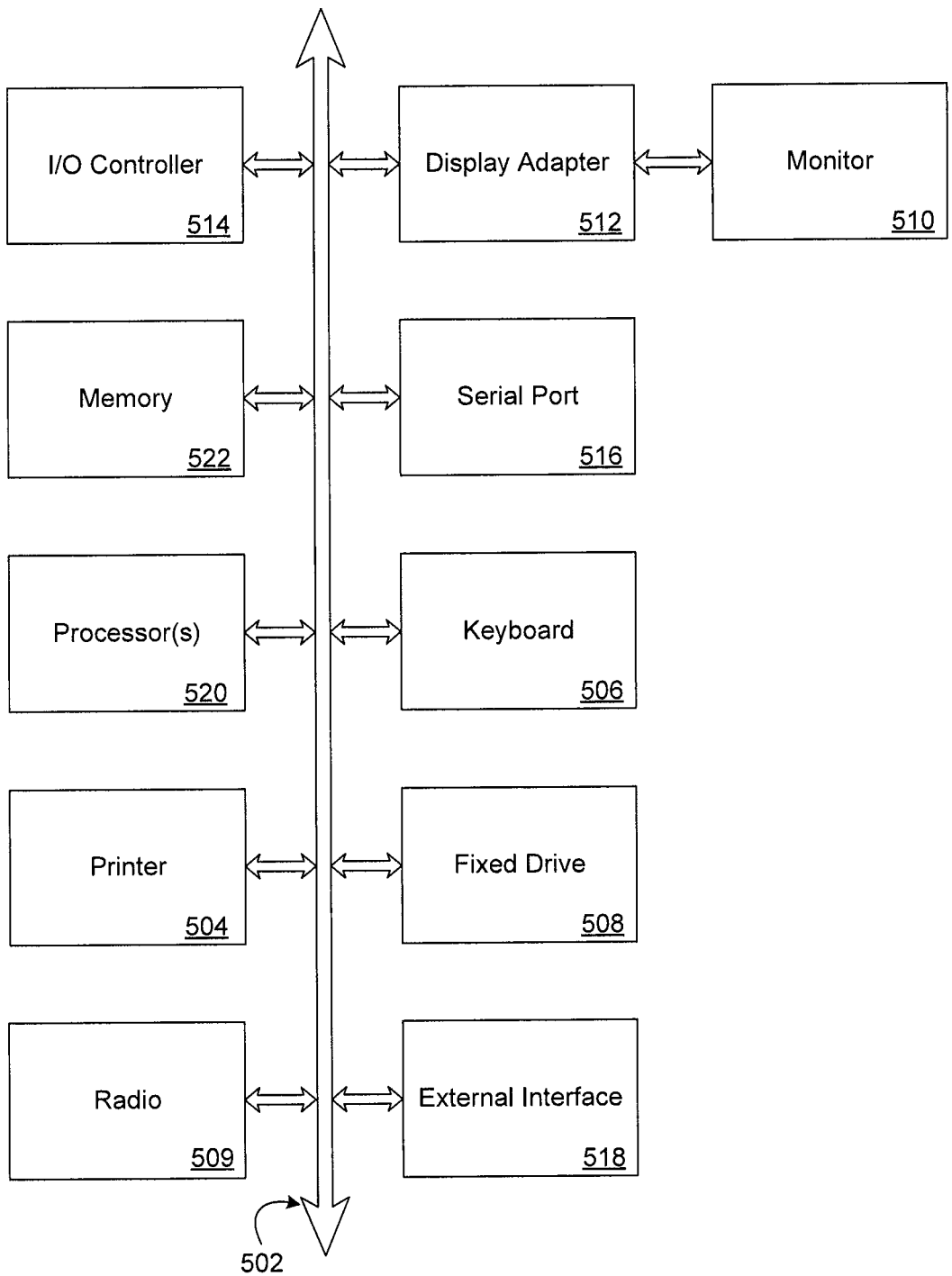
FIG. 5 is a diagram illustrating elements or components that may be present in a computer device or system configured to implement a method, process, function, or operation in accordance with an embodiment of the subject matter disclosed herein.

FIG. 5 is a diagram illustrating various computing elements or components that may be present in a computer device or system 500 configured to implement various computer methods, processes, functions, or operations as discussed above in accordance with various embodiments. The various subsystems shown in FIG. 5 are interconnected via a system bus 502. Additional subsystems may include a printer 504, a keyboard 506, a fixed drive 508, and a monitor 510, which is coupled to a display adapter 512. Peripherals and input/output (I/O) devices, which couple to an I/O controller 514, can be connected to the computer system by any number of means known in the art, such as a serial port 516. For example, the serial port 516 or an external interface 518 can be utilized to connect the computer device 500 to further devices and/or systems not shown in FIG. 5 including a wide area network such as the Internet, a mouse input device, and the like. Communication module may be a radio 509 set to the right frequency to enable communication between the elements and components of the system. The interconnection via the system bus 502 allows one or more processors 520 to communicate with each subsystem and to control the execution of instructions that may be stored in a system memory 522 and/or the fixed drive 508, as well as the exchange of information between subsystems. The system memory 522 and/or the fixed drive 508 may embody a tangible computer-readable medium.

It should be understood that the present disclosures as described above can be implemented in the form of control logic using computer software in a modular or integrated manner. Based on the disclosure and teachings provided herein, a person of ordinary skill in the art will know and appreciate other ways and/or methods to implement the present disclosure using hardware and a combination of hardware and software.

Any of the software components, processes or functions described in this application may be implemented as software code to be executed by a processor using any suitable computer language such as, for example, Java, Javascript, C++, PHP, or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

All references, including publications, patent applications, and patents, cited herein are hereby incorporated by reference to the same extent as if each reference were individually and specifically indicated to be incorporated by reference and/or were set forth in its entirety herein.

The use of the terms "a" and "an" and "the" and similar referents in the specification and in the following claims are to be construed to cover both the singular and the plural, unless otherwise indicated herein or clearly contradicted by context. The terms "having," "including," "containing" and similar referents in the specification and in the following claims are to be construed as open-ended terms (e.g., meaning "including, but not limited to,") unless otherwise noted. Recitation of ranges of values herein are merely indented to serve as a shorthand method of referring individually to each separate value inclusively falling within the range, unless otherwise indicated herein, and each separate value is incorporated into the specification as if it were individually recited herein. All methods described herein can be performed in any suitable order unless otherwise indicated herein or clearly contradicted by context. The use of any and all examples, or exemplary language (e.g., "such as") provided herein, is intended merely to better illuminate embodiments and does not pose a limitation to the scope of the disclosure unless otherwise claimed. No language in the specification should be construed as indicating any non-claimed element as essential to each embodiment of the present disclosure.

Different arrangements of the components depicted in the drawings or described above, as well as components and steps not shown or described are possible. Similarly, some features and sub-combinations are useful and may be employed without reference to other features and sub-combinations. Embodiments have been described for illustrative and not restrictive purposes, and alternative embodiments will become apparent to readers of this patent. Accordingly, the present subject matter is not limited to the embodiments described above or depicted in the drawings, and various embodiments and modifications can be made without departing from the scope of the claims below.

What is claimed is:

1. A method for determining turf conditions of turf grass across multiple turf grass locations, comprising:
    iteratively passing an electrical signal through one or more sensors disposed on a turf analysis device while the sensors are inserted into a plurality of respective turf locations;
    determining data about a first turf condition at each respective turf location using a processor disposed in the turf analysis device, the processor interpreting a signal from one of the sensors to determine the first turf condition stress indicator about the first turf condition;
    determining ambient temperature data about each respective turf location using the processor, the processor interpreting a signal from one of sensors to determine the ambient temperature data, the processor generating an ambient temperature turf stress indictor;
    collecting data about a plurality of stress indicators at the plurality of locations of turf using the turf analysis device;
    assimilating the collected data into a database of a computing device communicatively coupled to the turf analysis device;
    analyzing the collected data, at the computing device, to determine a plurality of turf stress indicators respectively corresponding to each of the plurality of locations in which data was collected;
    weighting each turf stress indicator wherein at least one of the turf stress indicators is weighted differently than another turf stress indicator;
    determining a turf performance indicator in response to determining each weighted turf stress indicator, the turf performance indicator indicative of the overall quality of the turf as influenced by each turf stress indicator; and
    communicating a recommended course of action in response to the determining the turf performance indicator.

2. The method of claim 1, wherein the determining the turf quality indicator further comprises:
    establishing a turf quality indicator algorithm; and
    calculating the turf quality indicator in response to collected data about the plurality of conditions at the plurality of locations.

3. The method of claim 1, wherein the determining the plurality of turf stress indicator further comprises determining at least one turf stress indicator corresponding to a condition corresponding to soil moisture level at one of the plurality of locations.

4. The method of claim 1, wherein the determining the plurality of turf stress indicators further comprises determining at least one turf stress indicator corresponding to a condition corresponding to salinity level at one of the plurality of locations.

5. The method of claim 1, wherein the determining the plurality of turf stress indicators further comprises determining at least one turf stress indicator corresponding to a condition corresponding to canopy temperature level at one of the plurality of locations.

6. The method of claim 1, wherein the determining the plurality of turf stress indicators further comprises determining at least one turf stress indicator corresponding to a condition corresponding to electrical conductivity to moisture ratio at one of the plurality of locations.

7. The method of claim 1, wherein the turf analysis device further configured to log information comprising at least one of the group comprised of: date, time, latitude, longitude, altitude, picture, and electronic notes.

8. The method of claim 1, wherein the turf performance indicator further comprises differently weighted influences from one or more turf stress indexes.

9. The method of claim 1, further comprising influencing the turf performance indicator based on a zone-to-zone comparison of historical turf performance index determinations.

10. The method of claim 1, further comprising influencing the turf performance indicator based on a geographic location-to-geographic location comparison of historical turf performance index determinations.

11. The method of claim 1, further comprising influencing the turf performance indicator based on a time period-to-time period comparison of historical turf performance index determinations.

12. A system for determining turf conditions of turf grass across multiple turf grass locations, comprising:
    a turf analysis device configured to collect data about a plurality of conditions of turf at a plurality of locations of turf using a plurality of electrically conductive sensors insertable into the turf;
a computing device communicatively coupled to the turf analysis device and configured to assimilate the collected data to a database;
an analysis module executable on the computing device and configured to analyze the collected data, at the computing device, to determine a plurality of turf stress indicators respectively corresponding to each of the plurality of conditions in which data was collected at each of the plurality of locations in which data was collected, wherein at least one condition comprises ambient temperature and at least one condition comprises a condition other than ambient temperature;
determine a turf performance indicator in response to determining each turf stress indicator, the turf performance indicator indicative of the overall quality of the turf as influenced by each turf stress indicator wherein at least one turf stress indicator is weighted differently than at least one other turf stress indicator in determining the turf performance indicator; and
generate a recommended course of action to a remote computing device in response to the determining the turf performance indicator.

13. The system of claim 12, further comprising a display coupled to the computing device and configured to display an animated representation of the plurality of locations showing turf performance indicators as determined by the analysis module.

14. The system of claim 12, further comprising a remote computing device communicatively coupled to the turf analysis device, the remote computing device configured to receive global position data collected from the turf analysis device and to send the global position data to the computing device.

15. The system of claim 12, wherein the turf performance indicator is further influenced by one of the group comprised of: weighting factors for each turf stress indicator, previously collected turf stress indicator data, related collected turf stress indicator data, and weather condition forecast data.

16. The system of claim 12, wherein the plurality of conditions comprises at least one of the group comprised of: moisture, electric conductivity, soil salinity, electrical conductivity to moisture ratio, and temperature.

* * * * *